United States Patent [19]

Crowell

[11] 4,424,362

[45] Jan. 3, 1984

[54] PROCESS FOR PREPARING A TRANS-6-PROPENYL BENZIMIDAZOLE

[75] Inventor: Thomas A. Crowell, Greenwood, Ind.

[73] Assignee: Eli Lilly and Company, Indianapolis, Ind.

[21] Appl. No.: 366,808

[22] Filed: Apr. 8, 1982

[51] Int. Cl.³ .......................................... C07D 235/30
[52] U.S. Cl. ................................................... 548/306
[58] Field of Search ........................................ 548/306

[56] References Cited

U.S. PATENT DOCUMENTS 4,174,454 11/1979 Paget et al. ......................... 548/306
4,230,868 10/1980 Paget et al. ......................... 548/306

*Primary Examiner*—Robert W. Ramsuer
*Attorney, Agent, or Firm*—Karen B. Dow; Arthur R. Whale

[57] ABSTRACT

This invention describes a process for selectively preparing trans-1-isopropylsulfonyl-2-amino-6-(1-phenyl-1-propenyl)benzimidazole by dehydrating the corresponding benzimidazole carbinol with certain specific acids.

3 Claims, No Drawings

PROCESS FOR PREPARING A TRANS-6-PROPENYL BENZIMIDAZOLE

BACKGROUND OF THE INVENTION

This invention concerns a process for preparing trans-1-isopropylsulfonyl-2-amino-6-(1-phenyl-1-propenyl)benzimidazole by dehydrating the corresponding benzimidazole carbinol with certain specific acids. The benzimidazole compound produced by the process is useful in suppressing the growth of viruses, particularly rhinoviruses, polio viruses, Coxsackie viruses, echo virus, and Mengo virus. The claimed process is stereoselective for the more active trans isomer.

A previous means of preparing an alkylidene benzimidazole, such as 1-isopropylsulfonyl-2-amino-6-(1-phenyl-1-propenyl)benzimidazole, involved dehydrating the corresponding 1-hydroxy-1-($C_1$-$C_7$ alkyl)benzyl derivative with p-toluenesulfonic acid to give a 50/50 mixture of cis and trans isomers. This is the expected mixture of an acid-catalyzed dehydration and such a process is described in U.S. Pat. No. 4,174,454.

Copending application, Ser. No. 366,760, filed of even date herewith, describes a series of 5- and 6-substituted-ethylenicbenzimidazole compounds.

SUMMARY OF THE INVENTION

The disclosed process selectively favors the preparation of the trans isomer of 1-isopropylsulfonyl-2-amino-6-(1-phenyl-1-propenyl)benzimidazole over the cis isomer. The selection is obtained by dehydrating the corresponding benzimidazole carbinol with certain specific acids.

DETAILED DESCRIPTION AND PREFERRED EMBODIMENT

The trans isomer is preferentially prepared by reacting the carbinol compound of formula

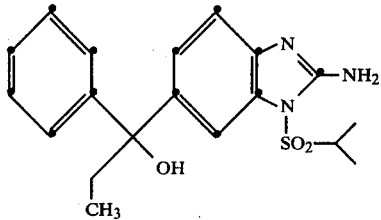

which is 1-isopropylsulfonyl-2-amino-6-(1-phenyl-1-hydroxy-1-propyl)benzimidazole, with certain acids, such as acetic acid, pyridyl hydrochloric acid, and boron trifluoride-ethyl ether.

The acid catalyzes the dehydration of the carbinol to form the alkylidene benzimidazole, 1-isopropylsulfonyl-2-amino-6-(1-phenyl-1-propenyl)benzimidazole. Dehydration involves the removal of a mole of water from each mole of carbinol to thus provide the corresponding alkylidene benzimidazole. The carbinol is combined with about an equal weight amount or an excess of the acid of up to about 20 times. The reaction can be carried out in an organic solvent such as chloroform, ethyl ether, benzene, dichloromethanes, or the like, unless the acid itself acts also as the solvent. The reaction may be conducted at a temperature from about 0° C. to about the reflux temperature of the particular solvent utilized for the reaction. Preferably the temperature of the reaction is from about 60° C. to reflux. Under these conditions, the dehydration typically is substantially complete within about one to about forty-eight hours. Longer reaction periods may be employed if desired. In particular, the reaction of acetic acid with 1-isopropylsulfonyl-2-amino-6-(1-phenyl-1-hydroxy-1-propyl)benzimidazole is conducted at about 60° C. overnight.

Upon completion of the dehydration reaction, the product benzimidazole generally may be isolated by simply washing the reaction mixture with a base, for instance dilute aqueous sodium bicarbonate or the like, and removing the organic reaction solvent by evaporation. Or the organic solvent can be stripped off by evaporation and then the remaining reaction mixture can be washed with a base, such as dilute aqueous sodium bicarbonate or the like. The product can be further purified if desired by normal methods, including chromatography and crystallization from solvents such as water, ethanol, ethyl acetate, acetone, heptane, and mixtures of these solvents. The preferred solvents of crystallization are heptane or methanol in water.

The isolation of pure trans isomer generally is accomplished by chromatography or by crystallization or fractional crystallization from solvents such as water, methanol, ethanol, acetone, and mixtures of these solvents.

The benzimidazole carbinol, which is the required starting material in the above-described dehydration reaction, is prepared by reaction of a 6-carbonyl substituted benzimidazole with a suitably substituted carbanion. The carbonyl benzimidazoles are available by the method of U.S. Pat. No. 4,118,742, which is incorporated by reference. The requisite carbanions are formed by reaction of an active methylene compound with a strong base such as methyl lithium, n-butyl lithium, lithium diisopropylamide, potassium tert.-butoxide, and the like. Active methylene compounds are those which have an electronegative functional group attached to a methyl or methylene group. Typical active methylene compounds which readily form carbanions include compounds of the formulas $CH_3CN$, $CH_3NO_2$, $CH_3SOC_1$-$C_4$ alkyl, $CH_3SO_2C_1$-$C_4$ alkyl, $CH_3SC_1$-$C_4$ alkyl, and the like. Such compounds generally are reacted with about an equimolar quantity or an excess of strong base in an unreactive organic solvent such as diethyl ether, tetrahydrofuran, dioxane, diglyme, and the like. Such reactions typically are carried out at a temperature of about $-78°$ to about $-50°$ C., and are substantially complete within about one to about six hours. Active methylene compounds which possess a functional group with acidic hydrogen atoms are preferably protected prior to reaction with a strong base. Typical protecting groups include silyl derivatives such as ethers and esters.

Once the carbanion has formed, it typically is not isolated, but rather is reacted in situ with a carbonyl benzimidazole derivative. The carbanion generally is utilized in an excess of about 1 to about 10 molar compared to the carbonyl benzimidazole, and the reaction is routinely carried out at a temperature of about $-70°$ to about 30° C. The product of the reaction is the aforementioned carbinol benzimidazole, and can be isolated by simply neutralizing the reaction mixture, for example with chilled ammonium chloride solution or dilute hydrochloric acid, and then removing the reaction solvent, for instance by evaporation under reduced pressure. Further purification of the carbinol benzimidazole generally is not needed, but if desired can be accomplished by routine procedures such as chromatography, crystallization, and the like.

Specifically the carbonyl benzimidazole, 1-isopropylsulfonyl-2-amino-6-benzoylbenzimidazole, is reacted with ethyl lithium to form the desired carbinol, 1-isopropylsulfonyl-2-amino-6-(1-phenyl-1-hydroxy-1-propyl)benzimidazole.

The 1-hydroxy-1-($C_1$–$C_7$ alkyl)benzyl derivatives, the carbinols, can also be prepared by reacting the corresponding carbonyl derivative with the appropriate Grignard reagent followed by hydrolysis. The carbonyl benzimidazole, 1-isopropylsulfonyl-2-amino-6-benzoylbenzimidazole, is reacted with ethylmagnesium bromide in anhydrous ethyl ether and then hydrolyzed to form the carbinol, 1-isopropylsulfonyl-2-amino-6-(1-phenyl-1-hydroxy-1-propyl)benzimidazole. The Grignard reagent, ethylmagnesium bromide, is made from ethylbromide and metallic magnesium in anhydrous ethyl ether.

The following examples are illustrative of this invention.

EXAMPLE 1

Four hundred ml of acetic acid was used to dissolve 19.15 g of the carbinol, 1-isopropylsulfonyl-2-amino-6-(1-phenyl-1-hydroxy-1-propyl)benzimidazole, and the mixture was stirred overnight at 60° C. The solution was stripped to dryness and the propylidene formed was 70% trans-1-isopropylsulfonyl-2-amino-6-(1-phenyl-1-propenyl)benzimidazole according to the NMR.

The trans isomer was then isolated by chromatography and crystallized from heptane. The yield was 4 g with 95% being trans isomer and less than 2% being cis isomer. The melting point was 140°–144° C.

EXAMPLE 2

One-half gram of the carbinol used in Example 1 and 1.5 g of the hydrochloride salt of pyridine were dissolved in 50 ml of chloroform, then heated to reflux for 16 hours. The NMR spectra indicated that 66% of the propylidene formed was the trans isomer.

EXAMPLE 3

One-half gram of the carbinol used in Example 1 and 0.33 ml of boron trifluoridie-ethyl ether complex were dissolved in 49 ml ethyl ether and refluxed for 4 hours. The solution was stripped to dryness and NMR indicated that 66% of the propylidene formed was the trans isomer.

I claim:

1. A process for preparing trans-1-isopropylsulfonyl-2-amino-6-(1-phenyl-1-propenyl)benzimidazole which comprises reacting 1-isopropylsulfonyl-2-amino-6-(1-phenyl-1-hydroxy-1-propyl)benzimidazole with acetic acid.

2. The process of claim 1 wherein the reaction is carried out at a temperature of about 60° C.

3. The process of claim 1 wherein the ratio of acid to benzimidazole is about 10 to 1.

* * * * *